United States Patent
Takahashi et al.

(10) Patent No.: US 9,766,090 B2
(45) Date of Patent: Sep. 19, 2017

(54) BODY MOVEMENT DETECTION DEVICE

(75) Inventors: Akihisa Takahashi, Lake Forest, IL (US); Hiroshi Ogawa, Nara (JP); Nobuki Yakura, Kyoto (JP)

(73) Assignee: OMRON HEALTHCARE CO., LTD., Muko-shi (JP)

( * ) Notice: Subject to any disclaimer, the term of this patent is extended or adjusted under 35 U.S.C. 154(b) by 793 days.

(21) Appl. No.: 13/351,887

(22) Filed: Jan. 17, 2012

(65) Prior Publication Data

US 2012/0116719 A1    May 10, 2012

Related U.S. Application Data

(63) Continuation of application No. PCT/JP2010/068034, filed on Oct. 14, 2010.

(30) Foreign Application Priority Data

Oct. 21, 2009  (JP) ................................. 2009-242105

(51) Int. Cl.
```
G01C 22/00    (2006.01)
G06F 15/00    (2006.01)
A61B 5/11     (2006.01)
A61B 5/00     (2006.01)
```

(52) U.S. Cl.
CPC .......... *G01C 22/006* (2013.01); *A61B 5/1112* (2013.01); *A61B 5/4866* (2013.01); *A61B 5/6823* (2013.01); *A61B 2562/0219* (2013.01)

(58) Field of Classification Search
CPC .......... G01C 22/006; A61B 2562/0129; A61B 5/4866; A61B 5/1112; A61B 5/6823; A61B 2562/0219

USPC ........................................................ 702/160
See application file for complete search history.

(56) References Cited

U.S. PATENT DOCUMENTS

| | | | |
|---|---|---|---|
| 6,546,336 B1 | 4/2003 | Matsuoka et al. | |
| 2005/0288852 A1* | 12/2005 | Kelly | ................... G01C 22/006 |
| | | | 701/465 |
| 2006/0020177 A1* | 1/2006 | Seo et al. | ...................... 600/300 |
| 2006/0020421 A1* | 1/2006 | Darley | ................. A43B 3/0005 |
| | | | 702/182 |
| 2006/0205566 A1* | 9/2006 | Watterson | ............... A63B 22/00 |
| | | | 482/8 |
| 2006/0230108 A1 | 10/2006 | Tatsuta et al. | |

(Continued)

FOREIGN PATENT DOCUMENTS

| | | |
|---|---|---|
| JP | A-9-53957 | 2/1997 |
| JP | A-2000-97722 | 1/2000 |

(Continued)

OTHER PUBLICATIONS

International Search Report dated Nov. 16, 2010 in International Application No. PCT/JP2010/068034 (with translation).

*Primary Examiner* — John Breene
*Assistant Examiner* — Peter Ngo
(74) *Attorney, Agent, or Firm* — Oliff PLC

(57) ABSTRACT

Information representing an activity intensity computed from a measured step count is transmitted from a first pedometer to a second pedometer as step count-related information. In the second pedometer, walking compatibility is determined based on the difference between the activity intensity in the first pedometer and the activity intensity in the second pedometer, and the determination result is displayed on both pedometers.

8 Claims, 17 Drawing Sheets

(56) References Cited

U.S. PATENT DOCUMENTS

| | | |
|---|---|---|
| 2007/0049462 A1* | 3/2007 | Asukai et al. .................... 482/8 |
| 2007/0208544 A1* | 9/2007 | Kulach et al. ................ 702/189 |
| 2009/0325766 A1* | 12/2009 | Kasama et al. .................. 482/8 |

FOREIGN PATENT DOCUMENTS

| | | |
|---|---|---|
| JP | A-2002-176426 | 6/2002 |
| JP | A-2003-319921 | 11/2003 |
| JP | A-2006-180899 | 7/2006 |
| JP | A-2006-293535 | 10/2006 |

\* cited by examiner

FIG. 5A

| Time | MA[METs] |
|---|---|
| 00'20" | 3 |
| 00'40" | 4 |
| 01'00" | 5 |
| 01'20" | 2 |
| ... | |

FIG. 5B

| Time | MB[METs] |
|---|---|
| 00'20" | 3 |
| 00'40" | 3 |
| 01'00" | 3 |
| 01'20" | 2 |
| ... | |

| \|MA-MB\| | Compatibility |
|---|---|
| 0 | 100 pts |
| 1 | 80 pts |
| 2 | 60 pts |
| 3 | 40 pts |
| 4 | 20 pts |
| ≥5 | 0 pts |

FIG. 9A
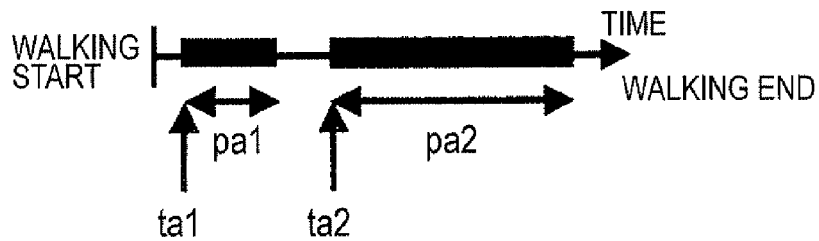
FIG. 9B
| TIME | PERIOD |
|---|---|
| ta1:00'20" | pa1:00'30" |
| ta2:01'00" | pa2:02'00" |
| ... | |
FIG. 9C
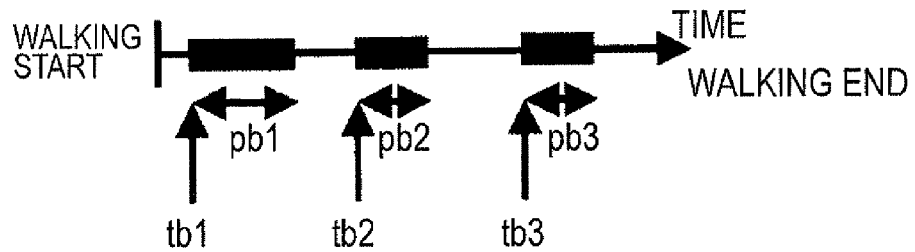
FIG. 9D
| TIME | PERIOD |
|---|---|
| tb1:00'20" | pb1:00'30" |
| tb2:01'00" | pb2:00'20" |
| tb3:02'00" | pb3:00'20" |
| ... | |

FIG. 13
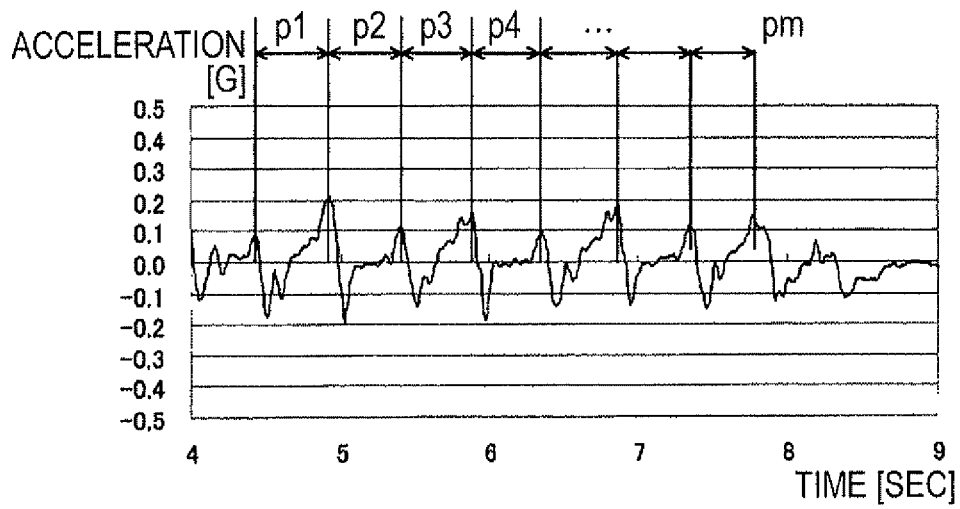
FIG. 14
| STABILITY RANKING | SD VALUE |
|---|---|
| A | <0.050 |
| B | ≥0.050 ~ 0.75 |
| C | ≥0.075 ~ 0.100 |
| D | ≥0.100 |
FIG. 15
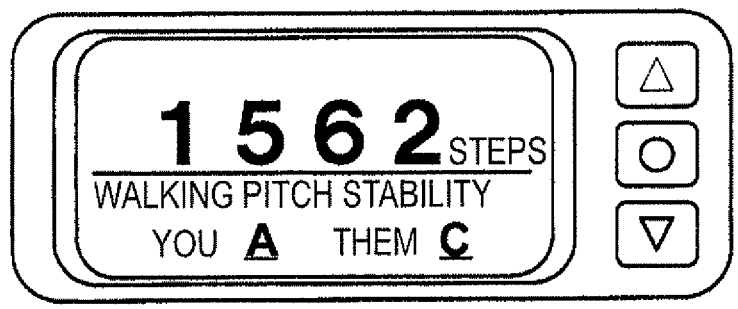

BODY MOVEMENT DETECTION DEVICE

TECHNICAL FIELD

The present invention relates to a body movement detection device, and more particularly to a body movement detection device with a communication function.

BACKGROUND ART

As part of health promotion, there are technologies that involve transmitting step count data in a pedometer to a server and sharing the information with a plurality of users, such as shown in JP 2002-176426A (hereinafter, Patent Literature 1), for example.

Also, as part of health promotion, the number of people going hiking in the mountains has been increasing in recent years. Map information and route information are extremely important for hiking, and there are techniques for obtaining map information and route information using, for example, a Garmin walking data logger or an activities of daily living analysis device disclosed in JP 9-53957A (hereinafter, Patent Literature 2) that plots a locus of movement on a map.

CITATION LIST

Patent Literature

Patent Literature 1: JP 2002-176426A
Patent Literature 2: JP 9-53957A

SUMMARY OF INVENTION

Technical Problem

However, communication in Patent Literature 1 involves transmission of the step count data from a pedometer to a server, and does not involve data being transmitted and received between pedometers.

Thus, there is a problem in that communication is restricted to merely sharing step count data via a server between users who partake in exercise such walking using a pedometer, and does not extend to sharing stimulating information based on the step count data that would maintain the user's motivation for their chosen form of exercise.

On the other hand, there is a problem in that the above-mentioned walking data logger is expensive and complicated to operate for users who go hiking. Also, even though past route information can be obtained with the device of Patent Literature 2, this information cannot be used as map information for hiking. Pedometers with an altimeter have a similar problem in that measurement information cannot be used as map information or route information for hiking.

The present invention has been made in view of such problems, and has as one object to provide a body movement detection device that is able to share, with another body movement detection device, stimulating information that is calculated based on acceleration data of both devices. Also, the present invention has as another object to provide a body movement detection device that is able to obtained map information and route information for hiking based on step count data in another body movement detection device.

Solution of Problem

According to one aspect of the present invention, the above objects are attained by a body movement detection device including an acceleration sensor, a computation unit for computing information related to body movement from acceleration data obtained by the acceleration sensor, a communication unit for communicating with another body movement detection device, a display processing unit for displaying, on a display device, information obtained from the body movement-related information and information related to body movement computed in the other body movement detection device and received from the other body movement detection device by the communication unit.

Preferably, the computation unit executes a calculation for computing an exercise intensity using the acceleration data, and a calculation for computing a value representing a correlation between an exercise intensity in the body movement detection device and an exercise intensity in the other body movement detection device, from an exercise intensity computed at a prescribed computation timing in the other body movement detection device and received as the body movement-related information from the other body movement detection device by the communication unit and an exercise intensity computed at a same timing as the computation timing in the other body movement detection device by the calculation for computing the exercise intensity, and the display processing unit displays, on the display device, a computation result of the calculation for computing the value representing, the correlation of the exercise intensities performed by the computation unit.

More preferably, the computation unit, in the calculation for computing the value representing the correlation of the exercise intensities, computes the value representing the correlation based on a difference between the exercise intensity in the other body movement detection device and the exercise intensity in the body movement detection device computed by the calculation for computing the exercise intensity.

More preferably, the computation unit, in the calculation for computing the value representing the correlation of the exercise intensities, computes the value representing the correlation, in a case where at least one of the exercise intensity in the other body movement detection device and the exercise intensity in the body movement detection device computed by the calculation for computing the exercise intensity differs from an exercise intensity at a time when exercise is not being undertaken.

Preferably, the computation unit further executes a calculation for computing a value representing a correlation between a duration of body movement in the body movement detection device and a duration of body movement in the other body movement detection device, from a duration of body movement computed to be at or above a prescribed exercise intensity in the other body movement detection device and received as the body movement-related information from the other body movement detection device by the communication unit and a duration of body movement in the body movement detection device computed to be at or above the prescribed exercise intensity by the calculation for computing the exercise intensity, and the display processing unit displays, on the display device, a computation result of the calculation for computing the value representing the correlation of the durations of body movement performed by the computation unit.

More preferably, the computation unit, in the calculation for computing the value representing the correlation of the durations of body movement, computes the value representing the correlation based on a percentage of overlapping time between the duration in the other body movement detection device and the duration in the body movement detection device obtained by the calculation for computing the exercise intensity in relation to measured time.

Preferably, the computation unit executes a calculation for computing a stability of pitch of body movement repeatedly detected from the acceleration data, and the display processing unit displays, on the display device, the stability of pitch of body movement in the body movement detection device computed by the calculation for computing the stability of pitch of body movement performed by the computation unit and the stability of pitch of body movement computed in the other body movement detection device and received from the other body movement detection device by the communication unit.

Preferably, the body movement detection device further includes an altitude measurement unit for measuring altitude, and the display processing unit displays, on the display device, as the information obtained from the body movement-related information in the body movement detection device and the body movement-related information received from the other body movement detection device, a correspondence between a step count or walking distance in the body movement detection device computed by the computation unit and an altitude measured by the altitude measurement unit, followed by a correspondence between a step count or walking distance and an altitude that are computed in the other body movement detection device and received from the other body movement detection device by the communication unit.

More preferably, the display processing unit displays a time required to walk to a preset point, based on the body movement-related information in the body movement detection device and the body movement-related information received from the other body movement detection device.

Advantageous Effects of Invention

According to the present invention, acceleration-based data can be transmitted and received mutually between pedometers. This data can then be used to share stimulating information among a plurality of users carrying pedometers. Also, the route information for walking exercises such as hiking can be obtained with a simple device, without performing complicated operations.

BRIEF DESCRIPTION OF DRAWINGS

FIG. 5A is a diagram showing a specific example of activity intensity information in a pedometer in the case of a first specific example.

FIG. 5B is a diagram showing a specific example of activity intensity information in another pedometer in the case of the first specific example.

FIG. 9A is a diagram showing a specific example of a computation result of activity intensity in a pedometer in the case of a second specific example.

FIG. 9B is a diagram showing a specific example of activity intensity information stored in the pedometer when the activity intensity of FIG. 9A has been computed in the case of the second specific example.

FIG. 9C is a diagram showing a specific example of a computation result of activity intensity in another pedometer in the case of the second specific example.

FIG. 9D is a diagram showing a specific example of activity intensity information stored in the other pedometer when the activity intensity of FIG. 9C has been computed in the case of the second specific example.

FIG. 13 is a diagram illustrating computation of the standard deviation of pitch in a pedometer according to the variation of the first embodiment.

FIG. 14 is a diagram showing a specific example of the correspondence relation between the standard deviation of pitch and the stability of pitch.

FIG. 15 is a diagram showing a specific example of display in the pedometer according to the variation of the first embodiment.

DESCRIPTION OF EMBODIMENTS

Hereinafter, embodiments of the present invention are described with reference to the drawings. In the following description, the same reference signs are given to the same components and constituent elements. The names and functions thereof are also the same.

First Embodiment

Figure 1A:
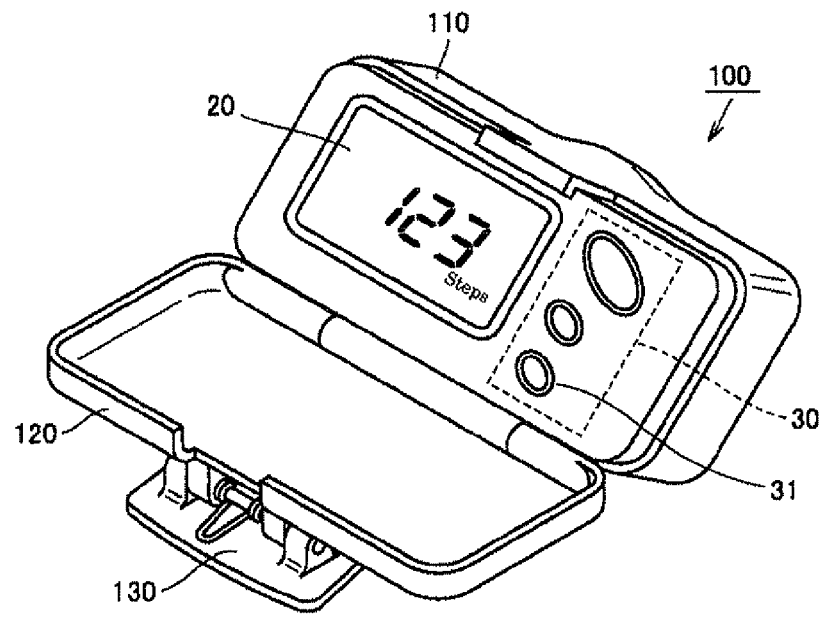
FIG. 1A is a diagram showing a specific example of the appearance of a pedometer according to an embodiment.

Referring to FIG. 1A, a pedometer 100 according to the first embodiment serving as a body movement detection device has a portable, compact main body easing, with the main body casing being divided into a case main body 110, a cover body 120, and a clip body 130.

The case main body 110 has a display surface on which are provided a display 20 capable of displaying various information such as the counted number of steps and the amount of calories burned and buttons 30 for receiving operations by a user. The buttons 30 include a communication button 31 for receiving instructions relating to communication with other pedometers described later.

Figure 1B:
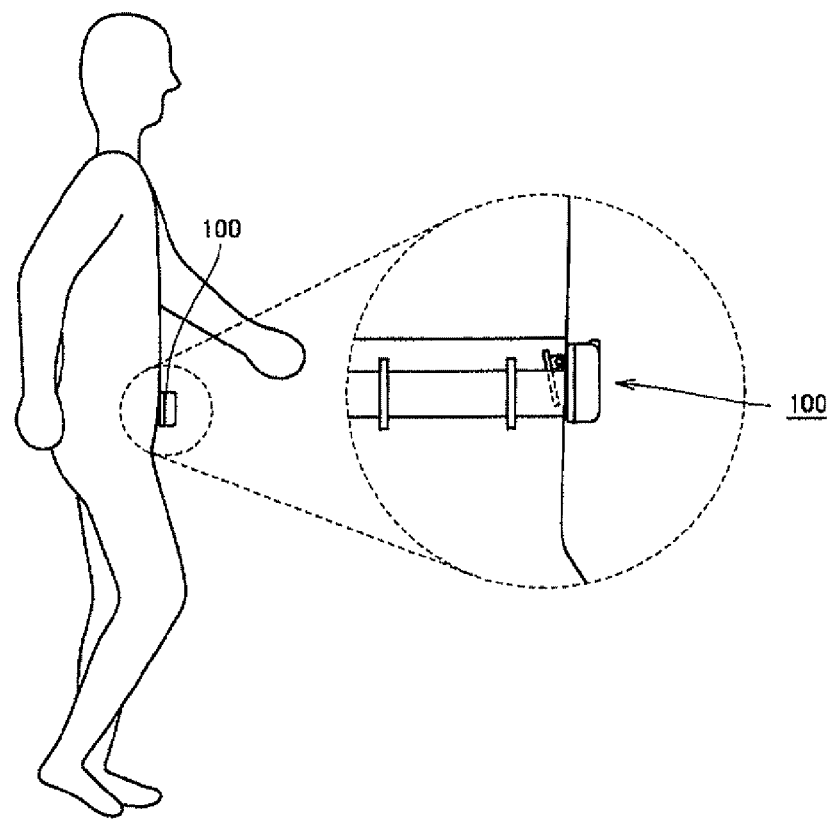
FIG. 1B is a diagram showing a specific example of wearing the pedometer according to an embodiment.

The bottom edge of the case main body 110 and the cover body 120 are rotatably coupled around a joining portion, and the pedometer 100 is opened and closed by rotation of the joining portion. The clip body 130 is provided on an opposite surface of the cover body 120 to the surface opposing the display surface of the case main body 110. The clip body 130 enables the pedometer 100 to be worn around the waist, abdomen or the like of the user as shown in FIG. 1B.

Figure 2:
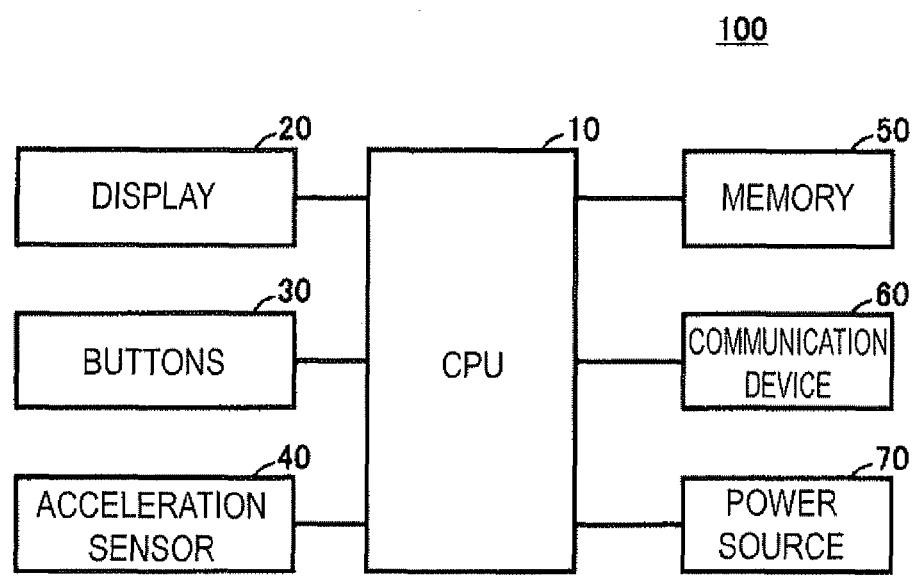
FIG. 2 is a diagram showing a specific example of a hardware configuration of the pedometer according to a first embodiment.

Referring to FIG. 2, the pedometer 100 includes, as an example of the hardware configuration, a CPU (Central Processing Unit) 10 for performing overall control, the above-mentioned display 20 and buttons 30, an acceleration sensor 40, a memory 50 for storing programs and the like that are executed by the CPU 10, a communication device 60 for communicating with other pedometers, and a power source 70 such as a battery.

Further, referring to FIG. 3, the pedometer 100 includes, as an example of the functional configuration, an acceleration detection unit 101 for detecting acceleration based on input from the acceleration sensor 40, a display unit 102 for controlling display on the display 20, a calculation unit 103 for performing calculations for compatibility determination described later, a power source connection unit 104 for performing processing to connect to the power source 70 and supply power to the entire device, a storage unit 105 for storing data and the like used for calculations in the calculation unit 103, an operation unit 106 for receiving input of operation signals from the buttons 30 and inputting required signals to the calculation unit 103, and a communication unit 107 for controlling communication in the communication device 60. These functions may be formed in the CPU 10 as a result of the CPU 10 reading out and executing programs stored in the memory 50, and at least a portion thereof may be constituted by hardware such as electrical circuitry.

Figure 4:
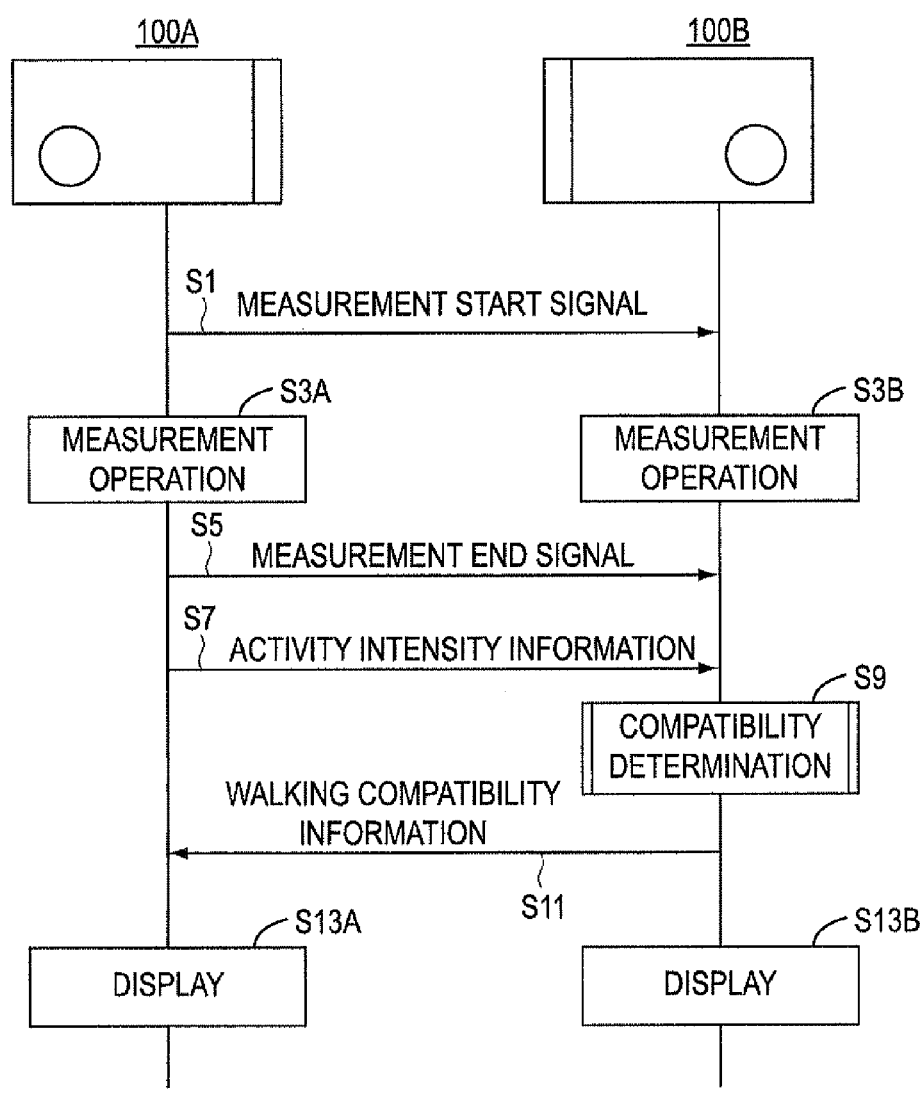
FIG. 4 is a diagram representing the operation flow in the pedometer according to the first embodiment.

The operation flow in the pedometer 100 according to the first embodiment is described using FIG. 4. In the first embodiment, compatibility determination is performed based on the acceleration data of two pedometers represented by pedometers 100A and 100B, for example. Here, "compatibility" is assumed to represent the correlativity of information relating to the actual amount of exercise obtained from the number of steps measured by two or more pedometers, rather than the correlativity of the number of steps itself. In view of this, "compatibility" is represented by the degree of compatibility, and the higher the value thereof, the higher the correlativity of the information relating to the amount of exercise, or in other words, the better the compatibility.

Referring to FIG. 4, as a result of the communication button 3 being pressed in the pedometer 100A serving as a first pedometer, a measurement start signal instructing the start of measurement is transmitted to the pedometer 100B by the communication device 60 of the pedometer 100A at step (hereinafter abbreviated to S) 1. Signal transmission to the pedometer 100B may be performed by a communication address being registered in the communication device 60 in advance, or by a signal transmitted within a communicable range from the communication device 60 being received by the communication device 60 of the pedometer 100E located in this range.

After transmission of the measurement start signal at S1, an operation for measuring the number of steps is performed in the pedometer 100A (S3A). An operation for measuring the number of steps is also performed the pedometer 100B that has received this signal (S3B). Here, this operation may be an operation for measuring the number of steps performed in a typical pedometer, one example of which involves counting each time an acceleration of at least a threshold is detected as one step.

As a first specific example of operations in the pedometer 100, in the calculation unit 103 of the pedometer 100A and the pedometer 100B, computation of activity intensity (METs) per unit time using the measured acceleration data is performed as the measurement operation, with a prescribed time interval (e.g., 20 sec interval) that is prescribed in advance as the unit of time. Activity intensity, which is an index representing the amount of exercise, is dependent on walking pitch (number of steps per unit time) and the input height of the user, and is computed in the calculation unit 103 using a known technique, such as the technique disclosed in JP No. 2009-28312A, for example. The computed activity intensity is stored in the storage unit 105 as activity intensity information in association with information specifying the computation timing.

As a result of the communication button 31 being pressed in the pedometer 100A during the step count measurement operation, a measurement end signal instructing the end of measurement is transmitted by the communication device 60 of the pedometer 100A to the pedometer 100B at S5. Here, transmission is similar to the transmission of S1.

After (or at the same time as) transmission of the measurement end signal at S5, activity intensity information is transmitted from the pedometer 100A to the pedometer 100E at S7. One example of activity intensity information is the activity intensity information stored in the storage unit 105. Note that activity intensity information may be transmitted from the pedometer 100A to the pedometer 100B whenever activity intensity is computed at 20 sec intervals. To simplify the processing and from the viewpoint of suppressing power consumption, however, it is assumed that activity intensity information preferably is transmitted after transmitting the measurement end signal at S5 as mentioned above.

The activity intensity computed at 20 sec intervals and the computation timing of FIG. 5A are assumed to be stored in the storage unit 105 of the pedometer 100A. Also, the activity intensity computed at 20 sec intervals and the computation timing of FIG. 5B are assumed to be stored by the storage unit 105 of the pedometer 100B. The calculation unit 103 of the pedometer 100B performs compatibility determination using the activity intensity information of these two pedometers at S9.

Figure 6:
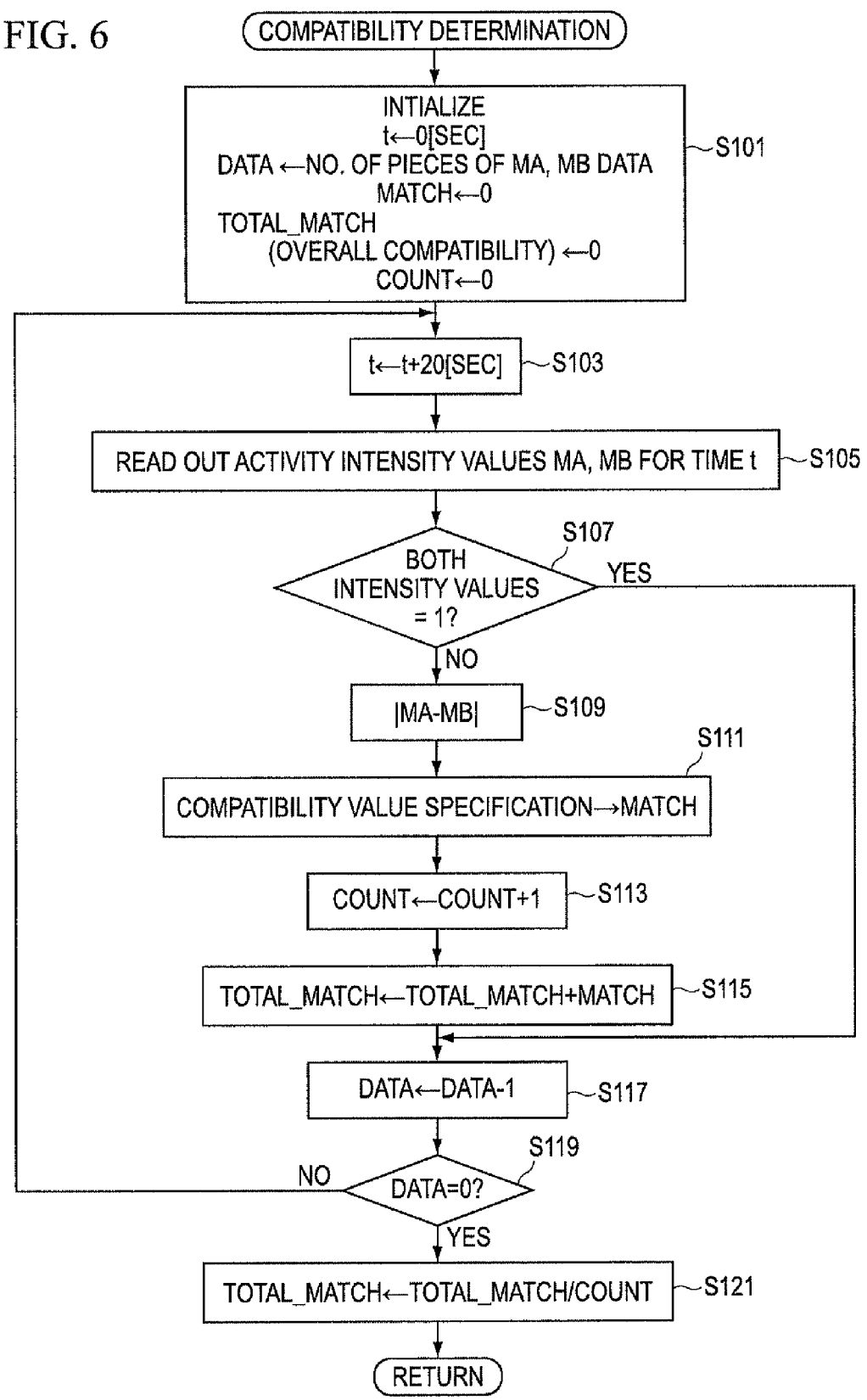
FIG. 6 is a flowchart showing a first specific example of compatibility determination processing in the pedometer according to the first embodiment.

Specifically, referring to FIG. 6, the calculation unit 103 at S101 initializes a variable "t" representing the computation timing of activity intensity, a variable "match" representing a compatibility value, a variable "total_match" representing an overall compatibility value, which is the total degree of compatibility, and a variable "count" for counting the number of calculations to 0. Also, a variable "data" representing the number of pieces of activity intensity data to be used in calculations is initialized to the number of pieces of activity intensity data for which the computation timing of the pedometer 100A and the computation timing of the pedometer 100B coincide. Thereafter, the calculation unit 103 at S103 sets the initial activity intensity computation timing by adding the computation timing interval "20" to the variable t, and at S105 respectively reads out the activity intensities MA and MB computed at that timing from the activity intensities of both pedometers.

Figures 7, 8:
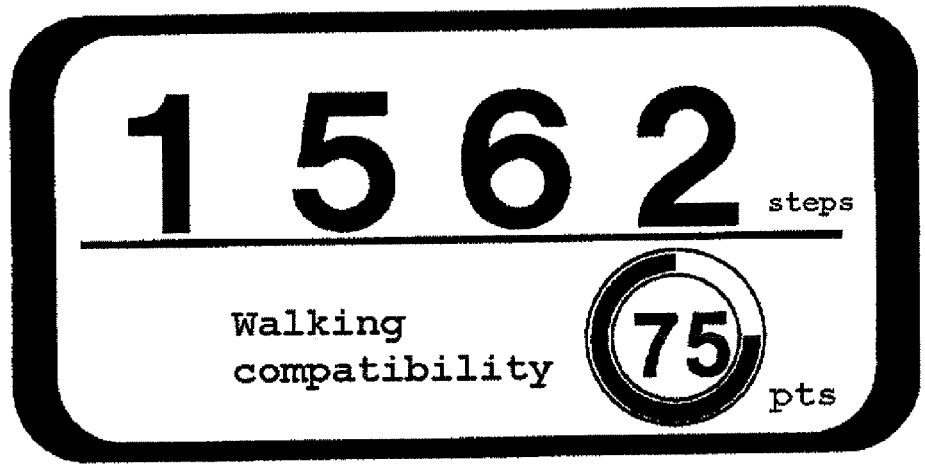
FIG. 7 is a diagram showing a specific example of a correspondence relation between differences in activity intensity and compatibility values.
FIG. 8 is a diagram showing a specific example of display in the pedometer according to the first embodiment.

Here, in the case where the read activity intensities MA and MB are both values (1 MET) representing a state in which exercise is not being undertaken (YES at S107), subsequent calculations are skipped and calculations corresponding to the next computation timing from the aftermentioned S117 onward are performed. When this is not the case (NO at S107), the calculation unit 103 at S109 computes the difference between the activity intensities MA and MB read out at S105, and at S111 specifies a compatibility value with reference to the table of FIG. 7 which is stored in advance in the storage unit 105. That is, as shown in FIG. 7, the correspondence relation between differences in activity intensities and compatibility values is stored in advance in the storage unit 105 in table form, for example. As an example, assume that larger compatibility values representing better compatibility the smaller the difference are stored, based on the idea that "walking compatibility is better the closer the activity intensities." The calculation unit 103 is able to specify the compatibility value corresponding to the computed difference, by referring to this table. The specified compatibility value is substituted into the variable "match".

Subsequently, the variable "count" is increment by 1 at S113, the variable "match" into which the specified compatibility value was substituted at S111 is added to the variable "total_match" at S115, and the variable "data" is decremented by 1 at S117. In the case where the variable "data" has not reached 0 at this point in time, that is, in the case where there is still activity intensity information to be used in calculations (NO at S119), the calculations from S103 onward are repeated, and a compatibility value based on the difference thereof is specified for every activity intensity computation timing in both pedometers (S111), and the sum thereof is computed (S115).

When the variable "data" reached 0, that is, when all the calculations for activity intensity information to be used in calculations have ended (YES at S119), the calculation unit 103 at S121 divides the variable "total_match" representing the sum of the compatibility values by the variable "count" representing the number of calculations, or in other words, computes the average value of the compatibility values to give the degree of compatibility.

When compatibility determination consisting of the above-mentioned series of operations ends in the calculation unit 103 of the pedometer 100E at S9, walking compatibility information including the computed degree of compatibility is transmitted to the pedometer 100A at S11.

When the walking compatibility information is received from the pedometer 100B, processing for displaying the degree of compatibility on the display 20 is performed by the display unit 102 of the pedometer 100A at S13A. After transmitting the walking compatibility information at S11, processing for displaying the degree of compatibility on the display 20 is also performed by the display unit 102 in the pedometer 100B at S13B. At S13A and S13B, as shown in FIG. 8, walking compatibility is thereby displayed along with the step count on the display 20 of both the pedometers 100A and 100B. Walking compatibility may be represented with a graph (e.g., pie chart, etc.), a level or the like such as shown in FIG. 8, rather than only a numerical value representing the computed degree of compatibility.

Calculations that compare data obtained from measured accelerations can thus be performed by communication between pedometers. Since activity intensity is, as mentioned above, an index of the amount of exercise that is dependent on walking pitch (number of steps per unit time) and height (length of stride), the correlativity of activity intensity may be high even in the case where walking exercises do not appear to be the same. According to the above calculations, the walking compatibility will be determined to be good in such cases. Accordingly, the users of the pedometers are each able to obtain information that cannot be obtained by comparing only the number of steps displayed on the pedometer, and are able to share an enjoyment of walking exercise that goes beyond merely comparing step counts. As a result, the pedometer is able to contribute to motivation support for walking exercise.

As a second specific example of operations in the pedometer 100, information on the exercise duration for which the activity intensity was at or above a prescribed intensity may be transmitted as activity intensity information from the pedometer 100A to the pedometer 100B at S7. Generally, since activity intensity at the time of walking exercise is said to be 3 METs, exercise that is being undertaken when an activity intensity of 3 METs or more is computed, for example, can be said to be a suitable level of walking exercise. In view of this, an activity intensity of 3 METs or more is given as an example of "at or above a prescribed intensity." Note that the "prescribed intensity" may be changeable by operation of the buttons 30 or the like. For example, input of a target activity intensity may be received as the "prescribed intensity."

In the case of the second specific example, the calculation units 103 of the pedometers 100A and 100B at S3A and S3B compute the activity intensity (METs) per unit time based on the measured number of steps or the like, with a prescribed time interval (e.g., 20 sec interval) that is prescribed in advance as the unit of time, and store the initial computation timing at which the activity intensity is 3 METs or more and the duration thereof in the storage unit 105 as activity intensity information.

Specifically, in the case where the result of computing the activity intensity in the pedometer 100A indicates that an activity intensity of at least 3 METs continued for periods pa1 and pa2 as shown in FIG. 9A, sets of information "Time" indicating the respective start timing of periods pa1 and pa2 (timing at which that activity intensity was initially computed) and information "period" indicating the respective durations thereof are stored in the storage unit 105 as activity intensity information, as shown in FIG. 9B. Similarly, in the case where the result of computing the activity intensity in the pedometer 100B indicates that an activity intensity of at least 3 METs continued for periods pb1, pb2 and pb3 as shown in FIG. 9C, sets of information "Time"

indicating the respective start timing of periods pb1, pb2 and pb3 (timing at which that activity intensity was initially computed) and information "period" indicating the respective durations thereof are stored in the storage unit 105 as activity intensity information, as shown in FIG. 9D.

Figure 10:
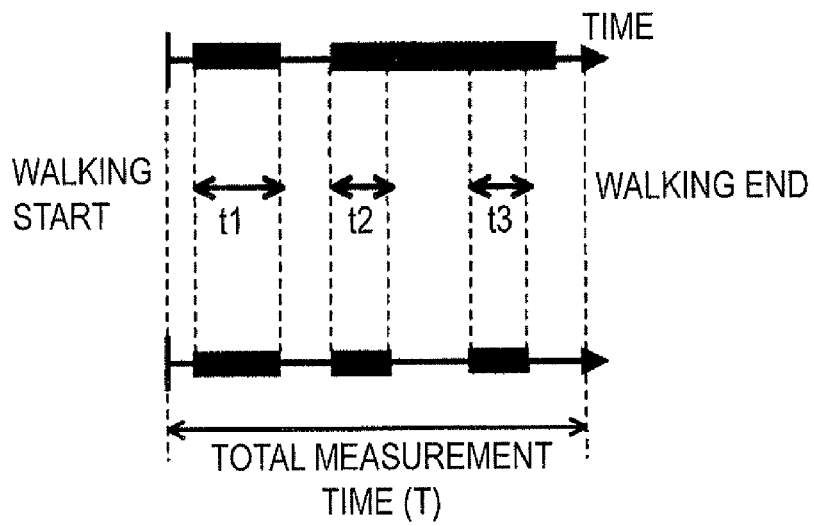
FIG. 10 is a diagram illustrating the second specific example of compatibility determination processing in the pedometer according to the first embodiment.

At S9, in the calculation unit 103 of the pedometer 100B, as shown in FIG. 10, periods t1, t2 and t3 for which an activity intensity of 3 METs or more was continued in both the pedometers 100A and 100B are specified through comparison of the periods pa1 and pa2 and the periods pb1, pb2 and pb3 specified in this information, and the percentage of the periods t1, t2 and t3 in relation to the total time for which the step count was measured is computed as the degree of compatibility.

Figure 11:
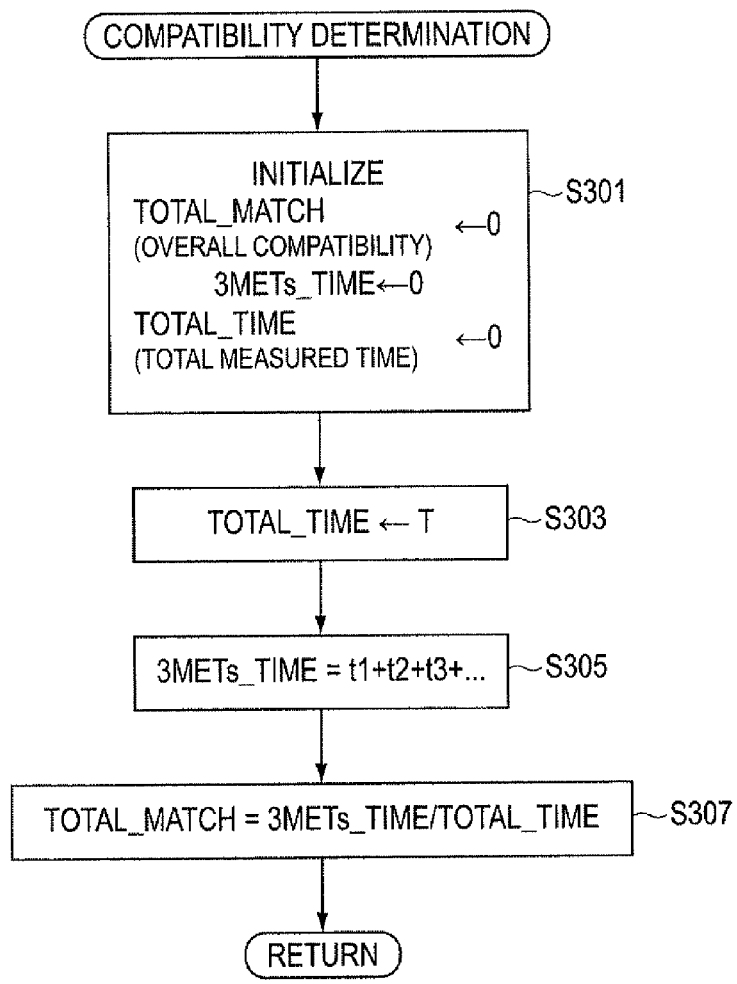
FIG. 11 is a flowchart showing a second specific example of compatibility determination processing in the pedometer according to the first embodiment.

Specifically, referring to FIG. 11, the calculation unit 103 at S301 initializes a variable "total_match" representing the overall compatibility value, which is the total degree of compatibility, a variable "3METs_time" representing the period for which an activity intensity of 3 METs or more was continued, and a variable "total_time" representing the total measurement time are initialized to 0. Thereafter, the calculation unit 103 at S303 reads out the total time T for which the step count was measured at S3A and S313, and substitutes the result into the variable "total_time".

The calculation unit 103 at S305 specifies the periods t1, t2, and t3 for which an activity intensity of 3 METs or more was continued in both the pedometers 100A and 100B through comparison of the activity intensity information of both the pedometers 100A and 100B, and substitutes the sum thereof into the variable "3METs_time." The calculation unit 103 at S307 then divides the period for which an activity intensity of 3 METs or more was continued by the variable "total_time" representing the total measurement time, that is, computes the percentage of the period for which an activity intensity of 3 METs or more was continued in relation to the total measurement time, and takes the result as the degree of compatibility.

As a result of calculations such as shown in the second specific example being performed, walking compatibility will be determined to be good in the case where there is high correlativity between the periods for which the walking exercises are performed at an activity intensity of 3 METs or more, which is said to be an effective level of exercise, even in the case where the walking exercises do not appear to be the same. Accordingly, users of the pedometers are each able to obtain information that cannot be obtained by comparing only the step count displayed on the pedometer, and are able to share an enjoyment of walking exercise that goes beyond merely comparing step counts.

Further, in the case of the second specific example, walking compatibility can be determined by simpler processing than the above-mentioned processing for determining walking compatibility based on differences in activity intensity.

Note that in the above first embodiment, as represented in FIG. 4, activity intensity information or exercise duration information is transmitted from the pedometer 100A to the pedometer 100B as a result of communication performed between the two pedometers 100A and 100B, compatibility determination is performed in the pedometer 100B, and the result is displayed on both pedometers. However, a personal computer, a server or the like can be used in addition to the pedometers 100A and 100B, as another exemplary configuration. That is, compatibility determination may be performed in the pedometer 100B, and the result may be transmitted from the pedometer 100B to a personal computer, a server or the like and stored in the server or the like.

In this case, the pedometer 100B receives information specifying a pedometer or information specifying the user carrying the pedometer together with the activity intensity information or exercise duration information from the pedometer 100A, and transmits the result of compatibility determination to the server or the like in association with the above specific information. At least the pedometer 100B out of the pedometers 100A and 100B can have a function of communicating with a server or the like. According to this configuration, even if each of a plurality of pedometers is not provided with the function of communicating with a server or the like, it is possible to store the result of compatibility determination between these pedometers if at least one of the pedometers has this function.

Variation

In the variation, a stability of pitch obtained from the acceleration data of two pedometers represented as pedometers 100A and 100B is computed as the compatibility determination. In the variation, "pitch" refers to the time required to step (each step) in a continuous walking movement. "Stability" of pitch refers to an index of whether or not variability in the time required for each step is within a prescribed range, and specifically refers to an index of whether the user is able to walk stably (at a steady rhythm). The stability of pitch can be taken as an index of compatibility. That is, in the case where the respective pitches measured by the pedometers 100A and 100E are stable, the users carrying the pedometers are considered to be walking comfortably at a similar speed, and "compatibility" can be judged to be good. On the other hand, in the case where at least one of the pitches measured by the pedometers 100A and 100B is not stable, the user carrying that pedometer is conceivably trying to match the walking speed of the other user, and "compatibility" can be judged to be poor.

Figure 12:
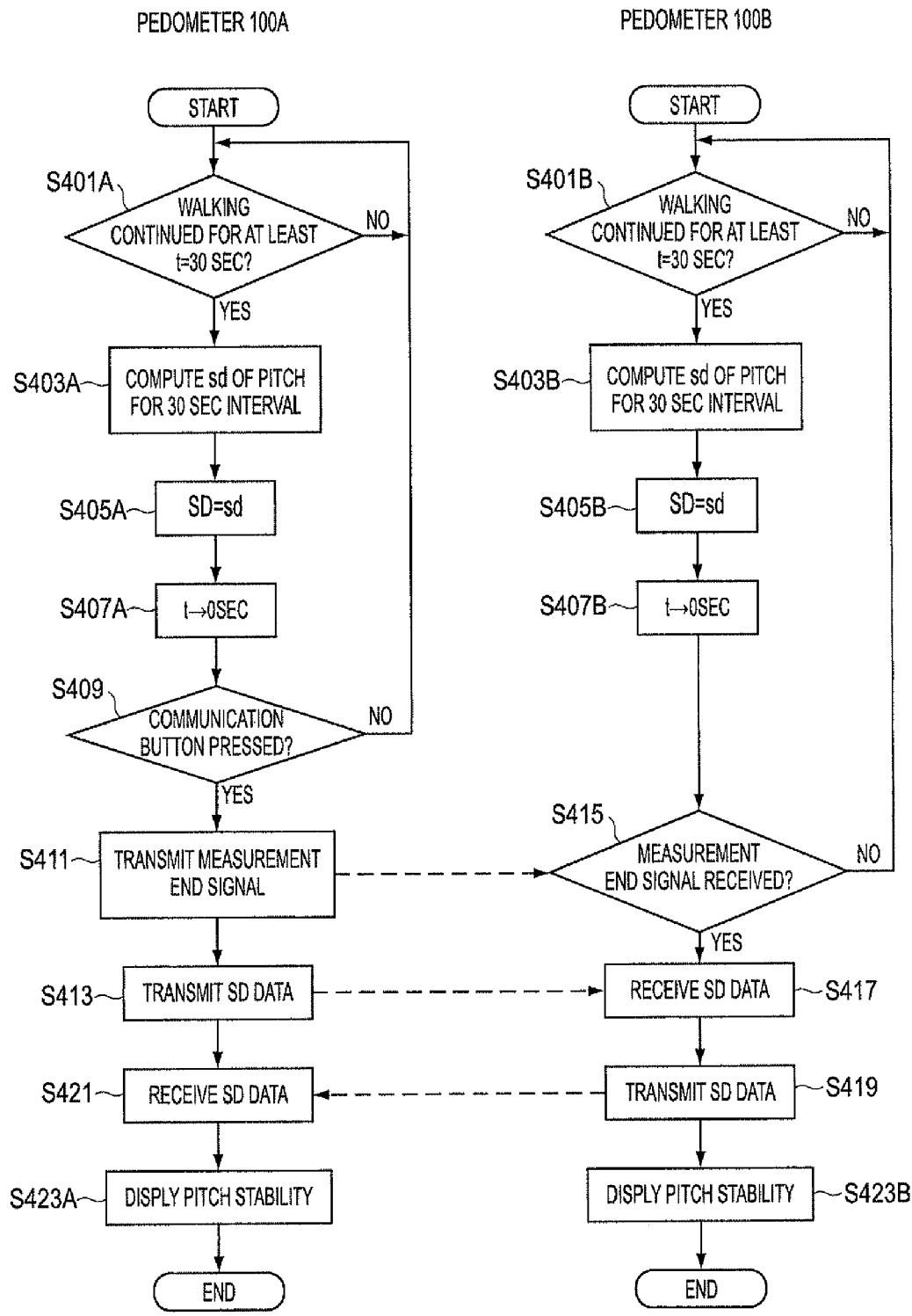
FIG. 12 is a flowchart showing a specific example of respective operations and the relation between the operations in two pedometers according to a variation of the first embodiment.

The pedometers 100A and 100B in the variation respectively execute the operations represented in FIG. 12. That is, referring to FIG. 12, in the pedometers 100A and 100B, the standard deviation (hereinafter, abbreviated to SD) per unit time of the measured pitch (time required for each step) is respectively computed as the measurement operation (S403A, S403B), with a prescribed time interval (e.g., 30 sec interval) that is prescribed in advance taken as the unit of time (YES at S401A, YES at S401B). At S403A and S403B, as represented in FIG. 13, the calculation unit 103 extracts the change in acceleration of single steps from the change in acceleration received from the acceleration sensor 40 during the 0 to 30 seconds for which time is counted with the variable t, specifies the respective times p1 to pm (m being a natural number) of the single steps, and computes the SD of the values p1 to pm. The calculation unit 103 stores the correspondence relation between SDs and stabilities (A-D) serving as values representing the stability of pitch in advance as represented in FIG. 14, and at S405A and S405B the stability corresponding to the computed SD is specified. Because the pitch when a person is walking is normally around 0.4 to 0.8 seconds, preferably a correspondence relation based on these values is stored by the calculation unit 103 of both pedometers. The specified stability is stored in the respective storage units 105 as SD data, and the above variable t is reset to 0 (S407A, S407B).

The measurement operation represented by S401A to S407A in the pedometer 100A is repeated (NO at S409) until the communication button 31 is pressed in the pedometer 100A during the step count measurement operation. When the communication button 31 is pressed (YES at S409), a measurement end signal instructing the end of measurement is transmitted to the pedometer 100B by the communication device 60 of the pedometer 100A at S411. After (or at the same time as) the measurement end signal is transmitted at S411, SD data is transmitted from the pedometer 100A to the pedometer 100B at S413. Also, SD data transmitted from the pedometer 100B is received at S421 as is discussed later.

The measurement operation represented by S401B to S407B in the pedometer 100B is repeated (NO at S415) until the measurement end signal is received from the pedometer 100A. When the measurement end signal is received from the pedometer 100A (YES at S415), SD data is subsequently received from the pedometer 100A at S417.

In the pedometers 100A and 100B, at S423A and S423B, the computed stabilities of pitch are displayed in both pedometers, based on the SD data of that pedometer and the received SD data, as represented in FIG. 15.

As a result of such operations being performed in the pedometers 100A and 100B and display such as shown in FIG. 15 being performed, it is possible to find out the walking state (stability of pitch) of other people in the case where walking exercise is being undertaken together by a plurality of users. A user carrying a pedometer can thereby compare the stability of their own pitch with the stability of another person's pitch, and judge whether the other person is walking within their limits (e.g., whether or not their own pace is too fast, etc.).

Also, in the case where the pitch is not stable, or in other words, in the case where stability is low, the user carrying the pedometer is also conceivably tired. Thus, another person's degree of fatigue can also be judged by referring to the stability of his or her pitch.

Second Embodiment

Figure 16:
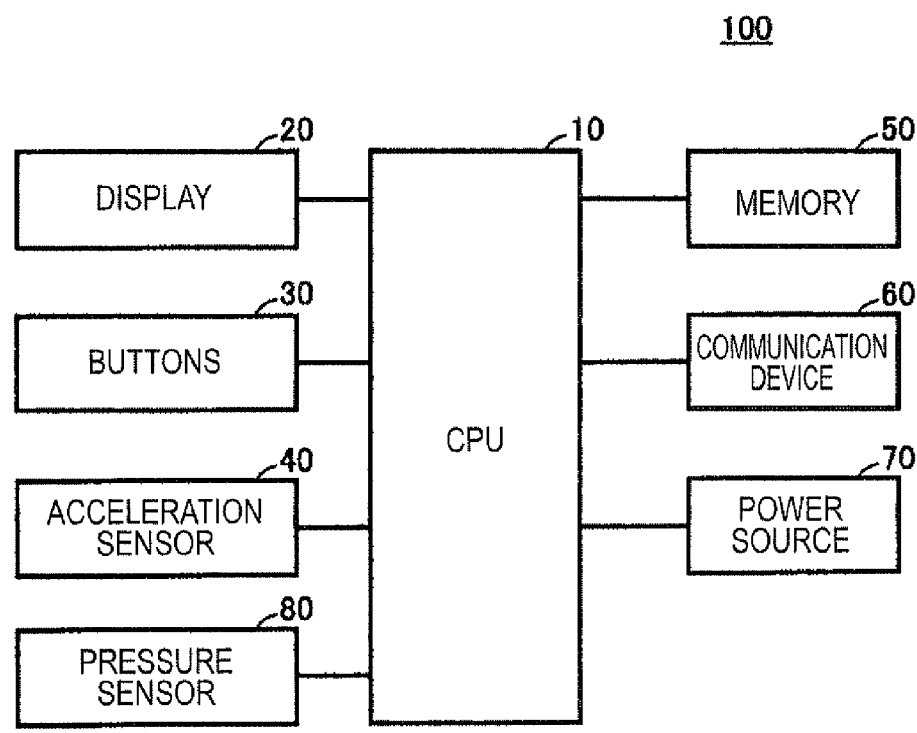
FIG. 16 is a diagram showing a specific example of a hardware configuration of a pedometer according to a second embodiment.

A pedometer 200 according to the second embodiment, in terms of appearance and method of attachment, is similar to that of the pedometer 100 according to the first embodiment represented in FIG. 1A and FIG. 1B. Referring to FIG. 16, the pedometer 200 includes a pressure sensor 80 in addition to the hardware configuration of the pedometer 100 shown in FIG. 2.

Figure 3:
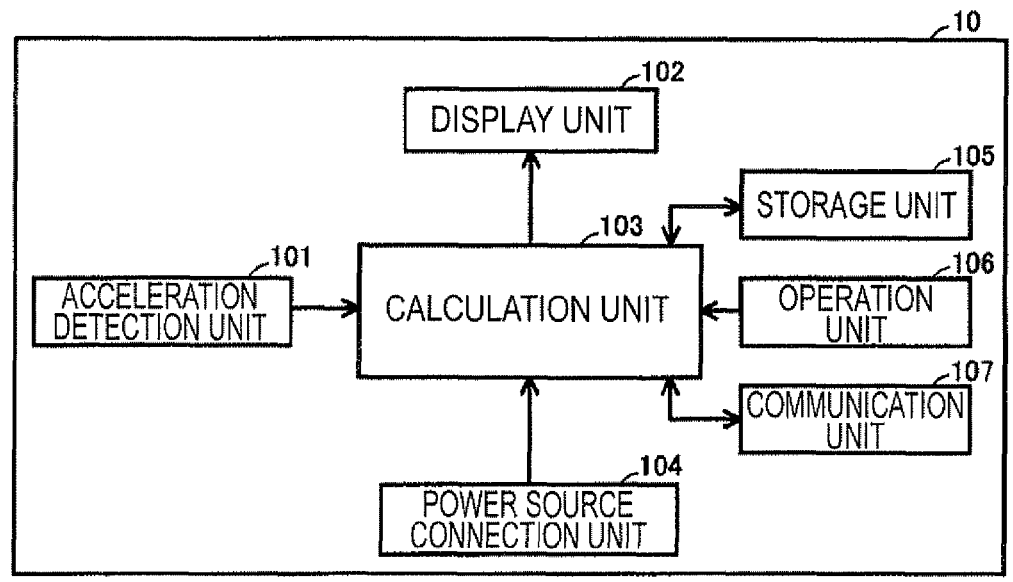
FIG. 3 is a diagram showing a specific example of a functional configuration of the pedometer according to the first embodiment.
Figure 17:
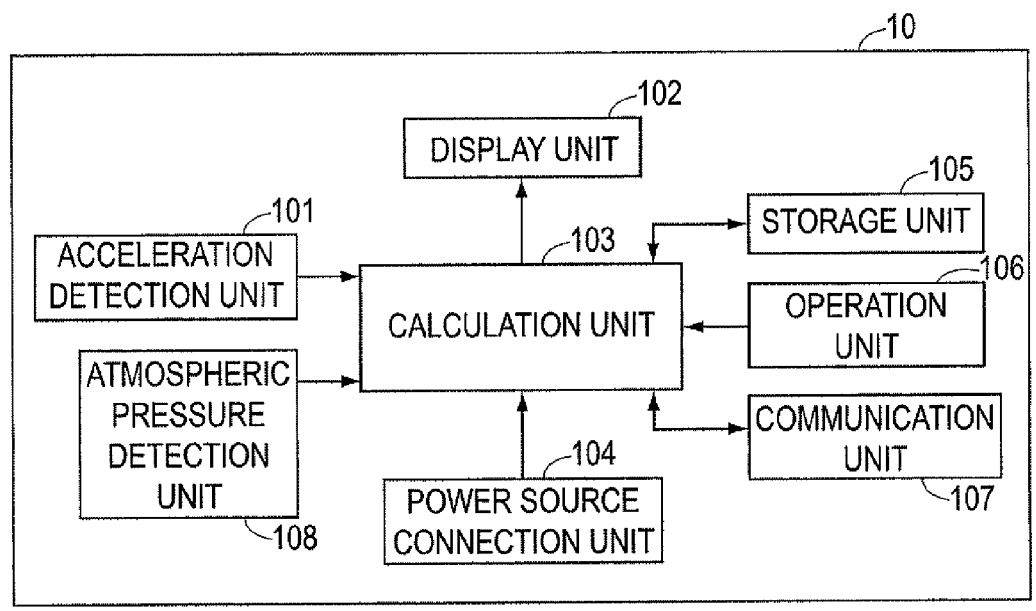
FIG. 17 is a diagram showing a specific example of a functional configuration of the pedometer according to the second embodiment.

Referring to FIG. 17, the pedometer 200 includes an atmospheric pressure detection unit 108 in addition to the functional configuration of the pedometer 100 shown in FIG. 3, as an example of the functional configuration. The functions shown in FIG. 17 may also be formed in the CPU 10 as a result of the CPU 10 reading out and executing a program stored in the memory 50, and at least a portion thereof may be constituted by hardware such as electrical circuitry. The atmospheric pressure detection unit 108 detects atmospheric pressure based on input from the pressure sensor 80. Based on this information, the calculation unit 103 computes the altitude.

Figure 18:
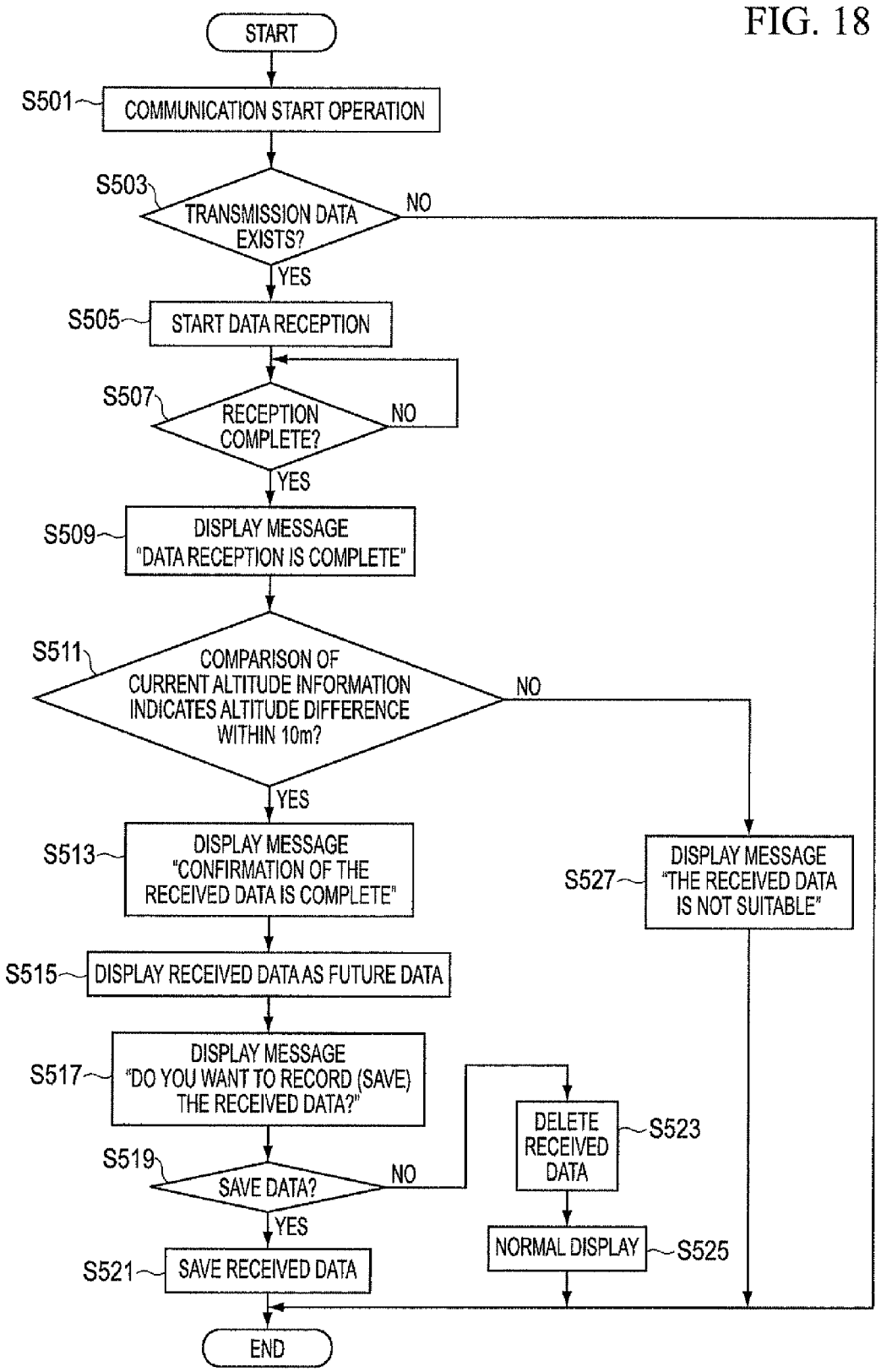
FIG. 18 is a flowchart showing a first specific example of operations in the pedometer according to the second embodiment.

A first specific example of the operation flow in the pedometer 200 according to the second embodiment is described using FIG. 18. In the second embodiment, in the case where the pedometer 200 communicates with another pedometer and satisfies a prescribed condition, an operation is performed for receiving the step count data of the other pedometer and displaying the received data as walking route information in combination with the step count data of the pedometer 200. Here, "walking route information" is altitude information representing a route obtained by taking the step count data of the pedometer 200 as a past walking route and the step count data of the other pedometer as a subsequent walking route.

Here, it is assumed that the pedometer 200 is carried by a user who goes hiking in the mountains. In the first specific example of operations, it is assumed that, in the case where the user meets another user going in the opposite direction along a walking route from the user's intended destination point (e.g., the summit of a mountain), operations are executed by performing communication, with the pedometer carried by the other user serving as the other pedometer. In view of this, the "walking route information" is assumed to be information representing the walking route from the hiking starting point to the destination point.

Referring to FIG. 18, subsequent operations start on receipt of input of an operation signal resulting from the communication button 31 having been pressed at S501. In this state, when data is transmitted from the other pedometer (YES at S503), reception of the data is started in the communication device 60 (S505). At least step count information measured by the other pedometer and altitude information are included as step count data in the data from the other pedometer.

When reception of the data is complete (YES at S507), a message notifying that reception is complete is displayed on the display 20 by the display unit 102 at S509.

Here, the calculation unit 103 compares the current altitude information included in the data received from the other pedometer with the current altitude information in the pedometer 200 detected by the atmospheric pressure detection unit 108. In the case where the altitude difference is a value that enables the altitude measurement function of the pedometer 200 and the altitude measurement function in other pedometer to be judged as being comparable, that is, a value within 10 m, for example, that enables the reliability of both altitude measurement functions to be confirmed (YES at S511), the calculation unit 103 judges the reliability of the data received from the other pedometer to be high. At this time, a message such as "Confirmation of the received data is complete" is displayed on the display 20 by the display unit 102 at S513 as a message notifying this fact. On the other hand, in the case where the above altitude difference is exceeded (NO at S511), the calculation unit 103 judges the reliability of the data received from other pedometer to be low. At this time, a message such as "The received data is not suitable" is displayed on the display 20 by the display unit 102 at S527 as a message notifying this fact, and the processing is ended without performing subsequent operations.

In the case where the reliability of the data received from the other pedometer is judged to be high, the calculation unit 103 at S515 performs a calculation for displaying the data received from the other pedometer as future data representing the subsequent walking route of the user carrying the pedometer 200, and causes the display unit 102 to perform display on the display 20. Specifically, since the data received from the other pedometer is data measured along the walking route from the destination point to the current location point of the user carrying the pedometer 200 in that order, the calculation unit 103 converts the received data to data oriented from the current location point to the destination point by reversing the measured values of the received data arranged in time series. The calculation unit 103 then concatenates the converted data to follow on from the data of the current location point in the step count data measured along the walking route from the starting point to the current location point and stored in the storage unit 105 of the pedometer 200. Step count data measured along the walking route from the starting point to the destination point is thereby generated.

Preferably, the pedometer 200 also receives from the other pedometer along with the step count data, data stored in the other pedometer indicating the other user's height. In this case, the calculation unit 103 corrects the step count data received from the other pedometer, based on the ratio of the height stored in the storage unit 105 of the pedometer 200 to the height stored in the other pedometer. Even in the case where the height of the user carrying the pedometer 200 and the height of the user carrying the other pedometer differ greatly, or in other words, where there is a difference in length of stride, the difference can be corrected and the received data can be approximated to information on the subsequent walking route of the user carrying the pedometer 200.

More preferably, the calculation unit 103 at S515 computes the required time to the destination point, based on the step count data received from the other pedometer, and causes the display unit 102 to also display this information. Specifically, in the case where data indicating walking time from the current location point to the destination point is included in the data received from the other pedometer, the calculation unit 103 causes the walking time specified by that data to be displayed as the required time. Alternatively, in the case where data indicating walking distance or step count from the current location point to the destination point as well as height is included in the data received from the other pedometer, the calculation unit 103 computes the required time by dividing the walking distance from the current location point to the destination point specified by that data by the walking speed of the user carrying the pedometer 200 obtained by measurement performed in the pedometer 200, and causes the display unit 102 to also display this information. Alternatively, in the case where altitude and walking time from the current location point to the destination point are included in the data received from the other pedometer, the calculation unit 103 performs correction by multiplying the ratio of the time required by the user carrying the pedometer 200 to walk to a prescribed altitude obtained by measurement performed in the pedometer 200 to the time required to walk to the prescribed altitude obtained from the received data by the walking time specified by the data received from the other pedometer, and causes this information to be displayed as the required time.

Note that the step count data received from the other pedometer preferably can be saved/deleted by a user operation. Specifically, a message such as "Do you want to store (save) the received data?", for example, is displayed on the display 20 by the display unit 102 at S517, as a message for prompting an operation as to whether to save the received data. In the case where an operation signal for saving the received data is received by the operation unit 106 (5519 at YES), the received data is saved to the storage unit 10 at S521. If this is not the case (5519 at NO), the received data is deleted at S523, after which normal screen display at the time of step count measurement is performed on the display 20 by the display unit 102 at S525.

For example, the calculation unit 103 of the pedometer 200 is able to perform the measurement operation by measuring the number of steps based on the signal from the acceleration detection unit 101 and the altitude for every prescribed number of steps based on the signal from the atmospheric pressure detection unit 108, and storing the step count and the altitude for every prescribed number of steps in the storage unit 105 as step count data. The pedometer 200 then receives, as step count data from the other pedometer as a result of the communication at S505, the step count and the altitude for every prescribed number of steps that were measured along the walking route from the destination point to the current location point of the user carrying the pedometer 200.

Figure 19A:
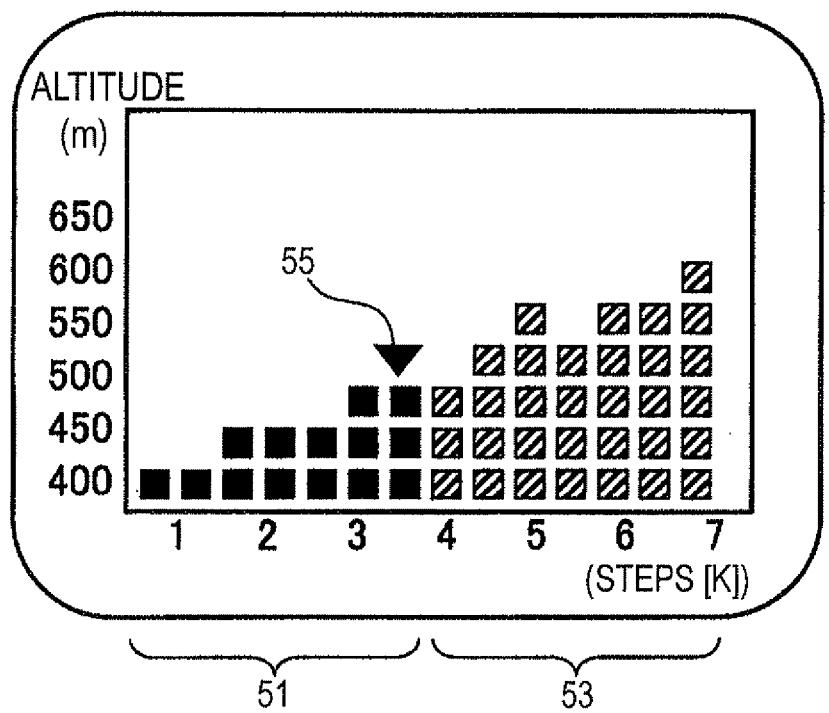
FIG. 19A is a diagram showing a specific example of display in the pedometer according to the second embodiment.

In this case, the display of FIG. 19A is performed at S515. That is, referring to FIG. 19A, altitude data for every unit number of steps based on the step count data stored in the storage unit 105 of the pedometer 200 is displayed in an area 51 and altitude data for every unit number of steps based on the step count data received from the other pedometer is displayed in an area 53, with step count shown on the horizontal axis and altitude shown on the vertical axis.

Figure 19B:
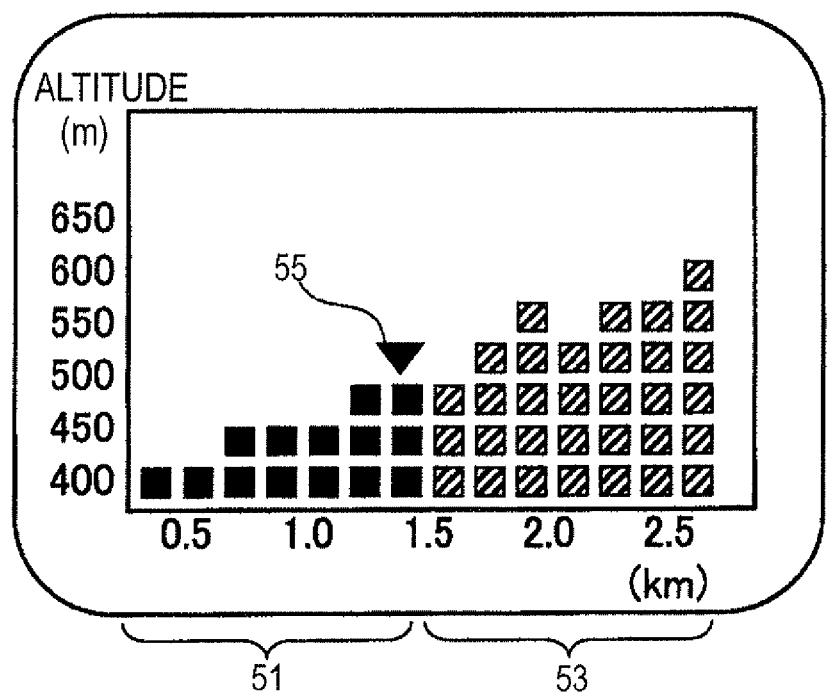
FIG. 19B is a diagram showing a specific example of display in the pedometer according to the second embodiment.

Also, as mentioned above, data indicating height or data indicating length of stride is stored in advance in each pedometer, and the pedometer 200 receives data indicating height or length of stride together with step count data from the other pedometer as a result of the communication at S505. In this case, the display of FIG. 19B may be performed at S515. That is, referring to FIG. 19B, walking distance may be computed by multiplying step count by length of stride in the calculation unit 103 in advance, and the altitude for every unit distance based on the step count data stored in the storage unit 105 of the pedometer 200 may be displayed in the area 51 and the altitude for every unit distance based on the step count data received from the other pedometer may be displayed in the area 53, with distance shown on the horizontal axis and altitude shown on the vertical axis.

Figure 20:
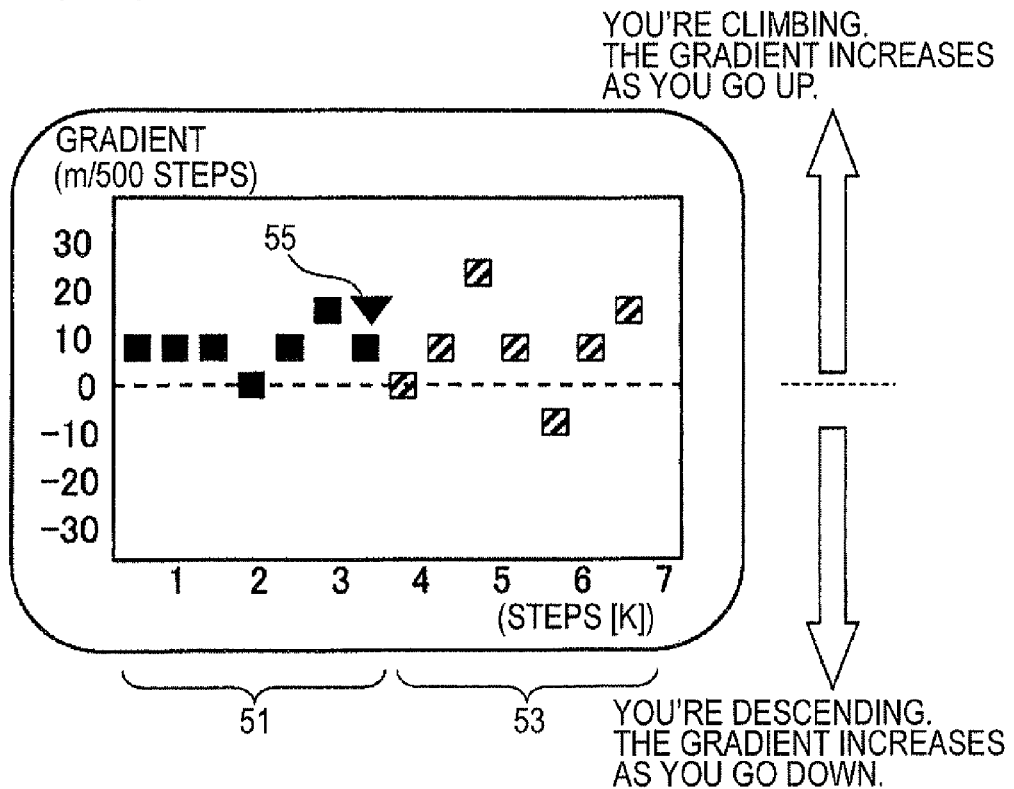
FIG. 20 is a diagram showing a specific example of display in the pedometer according to the second embodiment.

Alternatively, the display of FIG. 20 may be performed at S515. That is, referring to FIG. 20, gradient may be computed based on walking distance and altitude difference by multiplying step count by length of stride in the calculation unit 103 in advance, and the gradient per number of steps based on the step count data stored in the storage unit 105 of the pedometer 200 may be displayed in the area 51 and the gradient per number of steps based on the step count data received from the other pedometer may be displayed in the area 53, with step count shown on the horizontal axis and gradient shown on the vertical axis.

Figure 21:
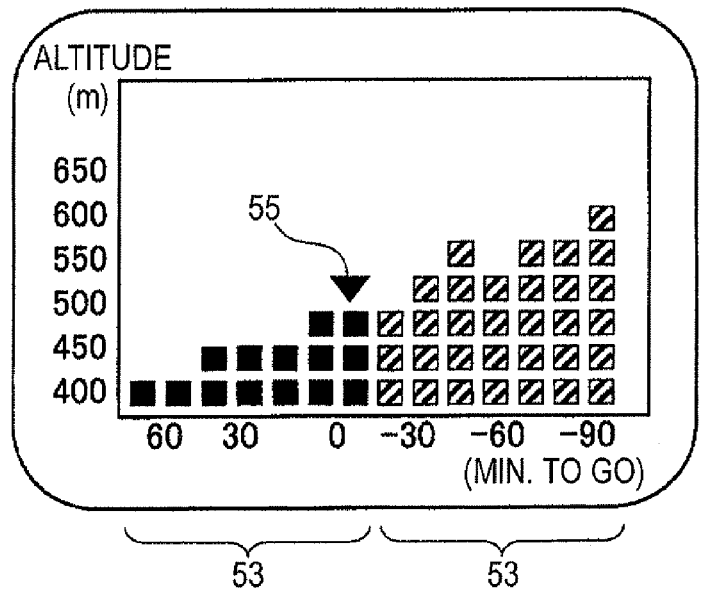
FIG. 21 is a diagram showing a specific example of display in the pedometer according to the second embodiment.

Also, the calculation unit 103 of the pedometer 200 is able to perform the measurement operation by measuring altitude at prescribed time intervals based on the signal from the atmospheric pressure detection unit 108, and storing the measurement timing and the altitude in the storage unit 105 as step count data. The pedometer 200 receives, as step count data from the other pedometer as a result of the communication at S505, the measurement timing and the altitude that were measured along the walking route from the destination point to the current location point of the user carrying the pedometer 200. In this case, the display of FIG. 21 is performed at S515. That is, referring to FIG. 21, the altitude for every unit time from the current time based on the step count data stored in the storage unit 105 of the pedometer 200 is displayed in the area 51 and the altitude data for every unit time from the current time based on the step count data received from the other pedometer is displayed in the area 53, with elapsed time from the current time shown on the horizontal axis and altitude shown on the vertical axis.

By performing display in this manner, altitude distribution or gradient distribution per number of steps, or in other words, per distance, or altitude distribution per elapsed time from the current time, from the starting point to the current location point and from current location point to the destination point are visually notified by the areas 51 and 53, respectively. Preferably, the display unit 102, as shown in FIG. 19A, FIG. 19B, FIG. 20 and FIG. 21, displays the step count data of the pedometer 200 and other step count data in different display modes or with a mark 55 representing the boundary therebetween. This allows the subsequent walking route from the current location point to the goal point to be readily grasped from the overall walking route. Also, the displayed subsequent walking route, being based on walking undertaken by another user carrying another pedometer and not on walking undertaken by the user himself or herself, can be clearly shown to be only a reference value. Further, in the case where the altitude distribution per elapsed time such as shown in FIG. 21 is displayed, in the first specific example the step count data from the other pedometer, being step count data for a walking route having the reverse gradient to the hiking gradient of the user carrying the pedometer 200, may possibly differ from the actual subsequent walking route of the pedometer 200. Thus, the step count data of the area 53 may be displayed without displaying time on the horizontal axis.

Figure 22:
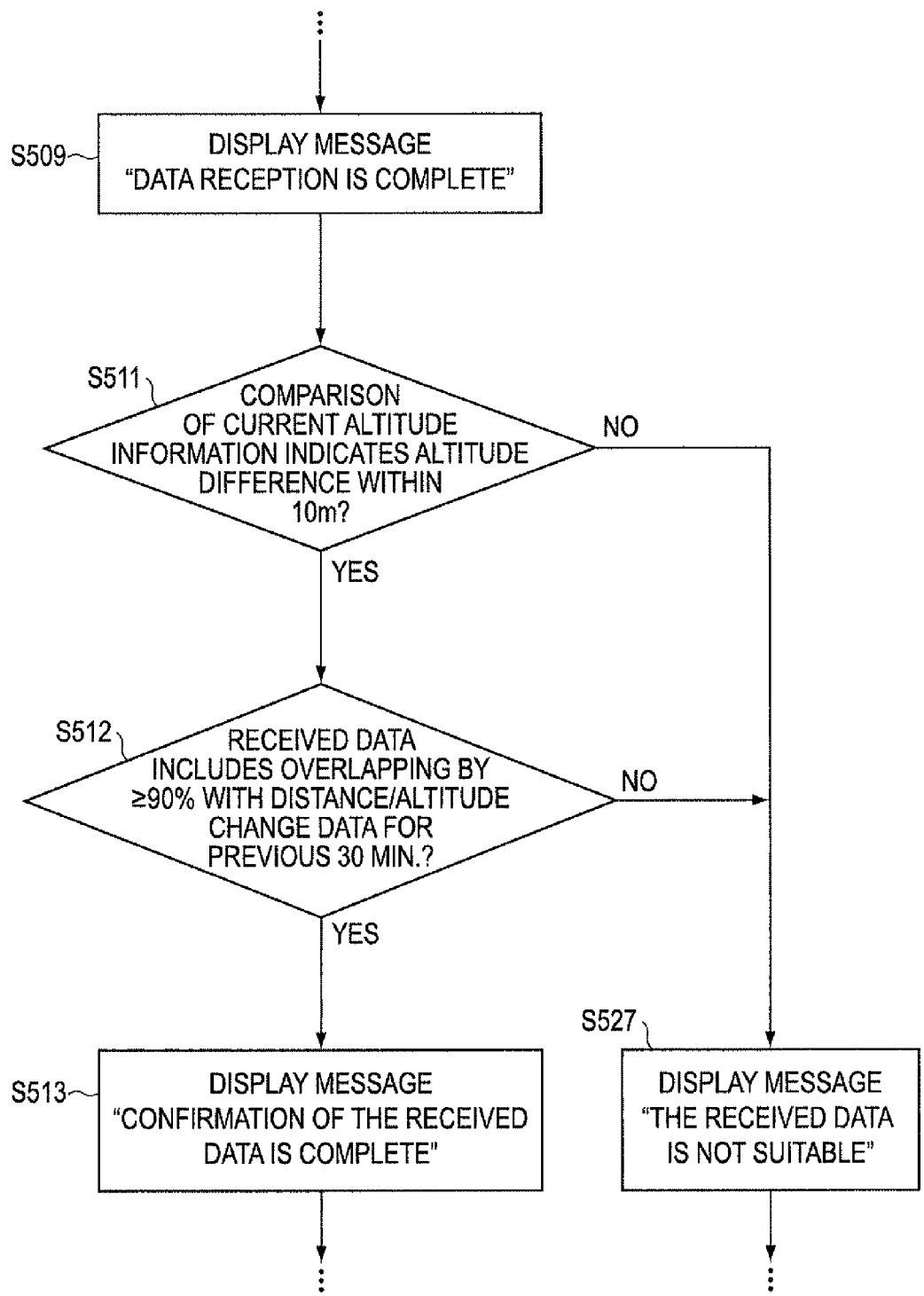
FIG. 22 is a flowchart showing a second specific example of operations in the pedometer according to the second embodiment.

Next, a second specific example of the operation flow in the pedometer 200 according to the second embodiment is described using FIG. 22. In the second specific example, it is assumed that, in the case where the user carrying the pedometer 200 meets another user who has already reached the destination point via the user's intended walking route and is thereafter coming back in the opposite direction along the walking route from the destination point, operations are executed by performing communication, with the pedometer carried by the other user serving as the other pedometer. In view of this, in the second specific example, after the operation of the first specific example confirming the reliability of the altitude measurement function of both pedometers, it is further confirmed whether the other pedometer has reached the destination point via the user's intended walking route and is thereafter performing measurement for the walking route going in the opposite direction along the walking route from the destination point, that is, it is confirmed that measurement is being performed for the same walking route as the user's intended route.

Specifically, referring to FIG. 22, in the second specific example, after confirming that the current altitude information included in the data received from the other pedometer and the current altitude information of the pedometer 200 detected by the atmospheric pressure detection unit 108 are within 10 m of each other (YES at S511), the calculation unit 103 further compares the data received from the other pedometer and the step count data stored in the storage unit 105 of the pedometer 200, and confirms whether the received data includes step count data that coincides with step count data stored in the storage unit 105 within a prescribed range. For example, step count data for the previous 30 minutes from the current point in time or step count data for the previous 450 m of walking distance from the current location point can be used as the user's step count data.

Figure 23:
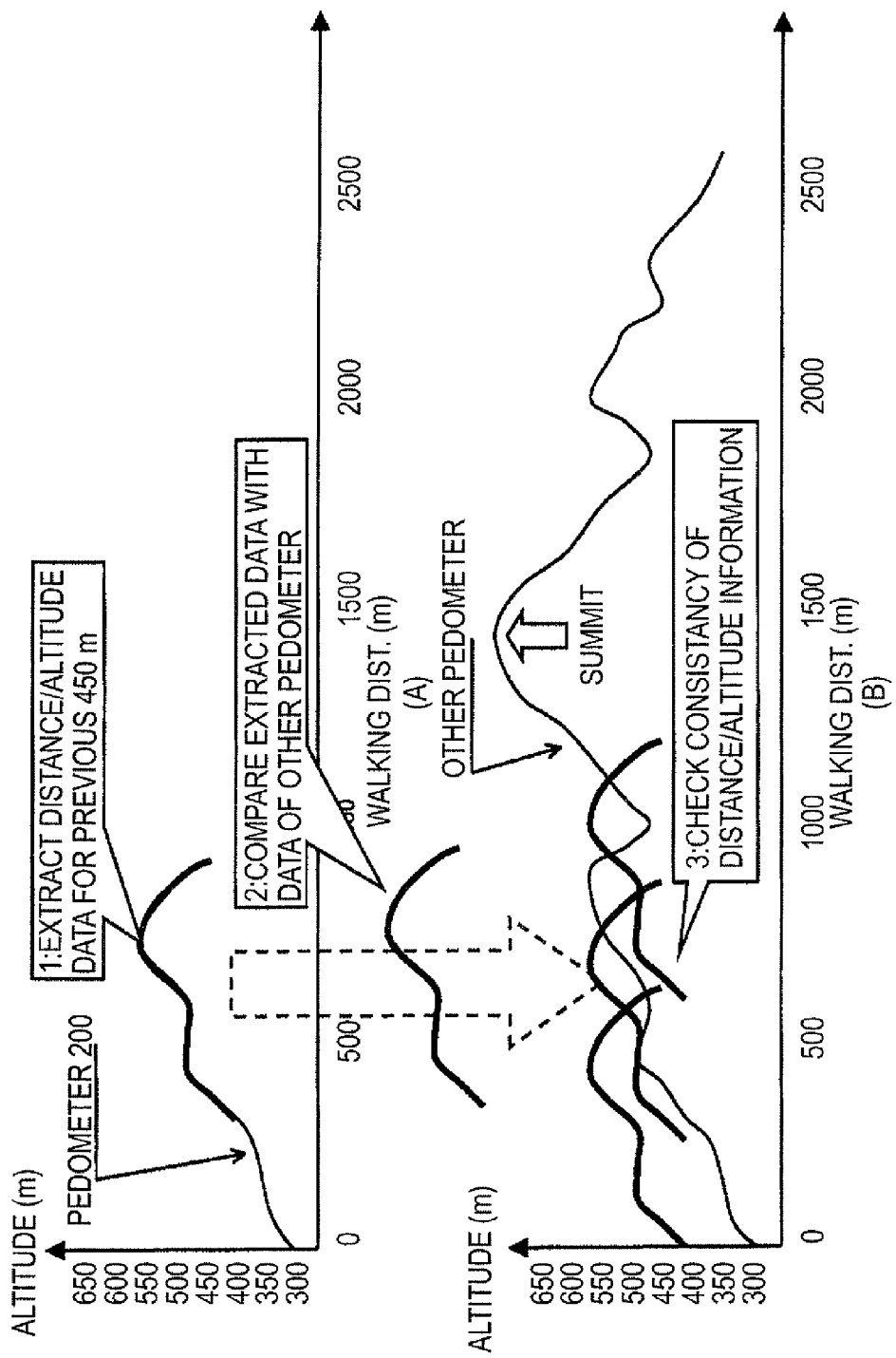
FIG. 23 is a diagram illustrating a method for confirming received data in the case of the second specific example.
Figure 24:
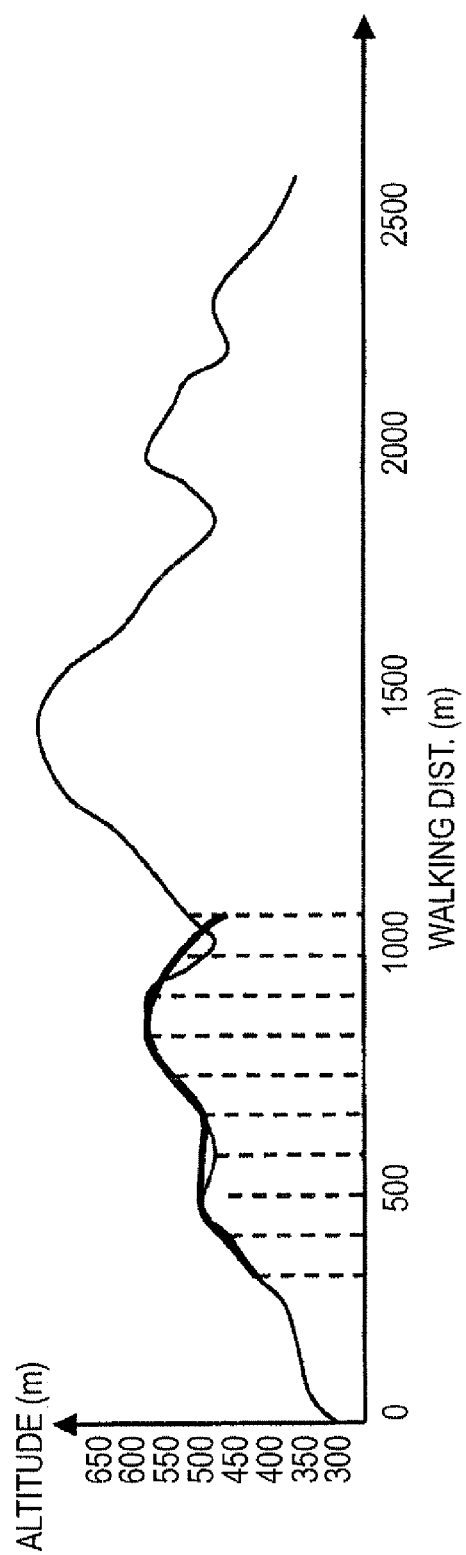
FIG. 24 is a diagram illustrating another method for confirming received data in the case of the second specific example.

Referring to FIG. 23, as one specific confirmation method, the calculation unit 103 uses a curve obtained with the walking distance and altitude for the previous 450 m of walking distance from the current location point included in the abovementioned step count data stored in the storage unit 105 as a template ((A) in FIG. 23) to match against a curve obtained with the walking distance and altitude included in the data received from the other pedometer ((B) of FIG. 23), and scans for data that coincides within a prescribed correlation range (e.g., ≥90%). Alternatively, referring to FIG. 24, as another confirmation method, the calculation unit 103 scans the step count data for the previous 30 minutes from the current point in time included in the abovementioned step count data stored in the storage unit 105, for altitudes at a prescribed walking distance interval (e.g., 50 m interval) which are included, in scanned order, within a certain range (e.g., ±10 m) of altitudes at the above walking distance intervals included in the data received from the other pedometer.

In the case where it is confirmed, as a result, that step count data corresponding to the received data is included (YES at S512), the calculation unit 103 judges that the data received from the other pedometer most likely results from measurement performed for the same walking route as the user's walking route. At this time, a message such as "Confirmation of the received data is complete" is displayed on the display 20 by the display unit 102 at S513 as a message notifying that fact. On the other hand, in the case where it is not confirmed that step count data corresponding to the received data is included (NO at S512), the calculation unit 103 judges that the data received from the other pedometer most likely does not result from measurement performed for the same walking route as the user's walking route. At this time, a message such as "The received data is not suitable" is displayed on the display 20 by the display unit 102 at S527 as a message notifying that fact, similarly to the case where the reliability of the data received from the other pedometer is judged to be low, and the processing is ended without performing subsequent operations.

In the case of the second specific example, when confirmation of the received data is complete as described above, in S515 step count data corresponding to the walking route from the current location point to the destination point included in the step count data received from the other pedometer is concatenated, as future data representing the walking route between these points, to follow on from the data of the current location point in the step count data measured along the walking route from the starting point to the current location point and stored in the storage unit 105 of the pedometer 200. Step count data measured along the walking route from the starting point to the destination point is thereby generated as a result using step count data obtained by the other pedometer for the same walking route as the pedometer 200, enabling more accurate route information to be presented.

The user is able to find route information with the pedometer that he or she is carrying without performing complicated operations during walking exercises such as hiking in the mountains, as a result of the operations shown in the first specific example or the second specific example being performed in the pedometer 200.

The embodiments disclosed herein are to be considered in all respects as illustrative and not restrictive. The scope of the invention is indicated by the claims rather than by the foregoing description, and all changes that come within the meaning and range of equivalency of the claims are intended to be embraced therein.

REFERENCE SIGNS LIST

10 CPU
20 Display
30 Buttons
31 Communication Button
40 Acceleration sensor
50 Memory
51, 53 Areas
55 Mark
60 Communication device
70 Power source
80 Pressure sensor
100, 100A, 100B, 200 Pedometers
101 Acceleration detection unit
102 Display unit 103 Calculation unit
104 Power source connection unit
105 Storage unit
106 Operation unit
107 Communication unit
108 Atmospheric pressure detection unit
110 Case main body
120 Cover body
130 Clip body

The invention claimed is:

1. A system comprising:
a first body movement detection device to be carried by a first user; and
a second body movement detection device to be carried by a second user, the first body movement detection device and the second body movement detection device being configured to communicate with each other over a network, the first body movement detection device comprising:
  a first acceleration sensor configured to generate first acceleration data of the first user;
  a first communication unit configured to transmit and receive a signal to and from the second body movement detection device;
  a first button configured to receive an operation by the first user for generating a start time and an end time; and
  a first processor configured to:
    upon receipt, via the first button, of the operation by the first user for generating the start time and the end time:
      control the first communication unit to transmit, over the network, the start time and the end time to the second body movement detection device, so that the start time and the end time initiated initiated by the first body movement detection device are commonly used between the first body movement detection device and the second body movement detection device;
      compute a first activity intensity related to a body movement of the first user based on the generated first acceleration data obtained in a common period determined by the start time and the end time;
      control the first communication unit to transmit, over the network, the first activity intensity to the second body movement detection device;
      receive, via the first communication unit, a second activity intensity in the common period transmitted over the network from the second body movement detection device, wherein the second body movement device computes the second activity intensity during the common period based on the start time and the end time received from the first body movement detection device;
      determine a compatibility of the first user and the second user based on a comparison of the first activity intensity and the second activity intensity both of which are obtained in the common period; and
      output, to a display, information related to the determined compatibility of the first user and the second user.

2. The system according to claim 1, wherein the first processor is further configured to compute the compatibility based on a difference between the second activity intensity and the first activity intensity.

3. The system according to claim 1, wherein the first processor is further configured to compute the compatibility, when at least one of the second activity intensity and the first activity intensity differs from a predetermined activity intensity taken at a time when exercise is not being undertaken.

4. The system according to claim 1, wherein the first processor is further configured to:
  calculate a value representing a correlation between a first duration of body movement in the first body movement detection device and a second duration of body movement in the second body movement detection device, when a duration of the first duration and/or second duration is computed to be at or above a prescribed activity intensity level, and
  control the display to display a computation result of the calculation for computing the value representing the correlation of the first and second durations of body movement performed.

5. The system according to claim 1, wherein the first processor is further configured to compute the compatibility based on a percentage of time in which the first and second exercise intensities are both above a threshold value divided by a measured time.

6. The system according to claim 1, wherein the first processor is further configured to:
  calculate a first stability of pitch of body movement repeatedly detected from the acceleration data, and
  control the display to display the calculated first stability of pitch of body movement in the first body movement detection device, and a second stability of pitch of body movement computed in the second body movement detection device and received from the second body movement detection device by the first communication unit.

7. The system according to claim 1, further comprising an altitude measurement unit for measuring a first altitude, wherein the first processor is further configured to control the display to display a correspondence between a first step count or walking distance in the first body movement detection device and the first altitude measured by the altitude measurement unit, followed by a correspondence between a second step count or walking distance and a second altitude that are computed in the second body movement detection device and received from the second body movement detection device by the first communication unit.

8. The system according to claim 7, wherein the first processor is further configured to control the display to display a time required to walk to a preset point, based on the first acceleration data, and the second acceleration data.

* * * * *